United States Patent
Atiya et al.

(10) Patent No.: US 10,743,967 B2
(45) Date of Patent: *Aug. 18, 2020

(54) APPARATUS AND METHOD FOR MEASURING SURFACE TOPOGRAPHY OPTICALLY

(71) Applicant: Align Technology, Inc., San Jose, CA (US)

(72) Inventors: Yossef Atiya, Maccabim (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/287,120

(22) Filed: Feb. 27, 2019

(65) Prior Publication Data
US 2019/0262108 A1 Aug. 29, 2019

Related U.S. Application Data

(63) Continuation of application No. 15/811,365, filed on Nov. 13, 2017, now Pat. No. 10,258,437, which is a (Continued)

(51) Int. Cl.
*A61C 9/00* (2006.01)
*A61B 5/00* (2006.01)
(Continued)

(52) U.S. Cl.
CPC ........ *A61C 9/0066* (2013.01); *A61B 1/00009* (2013.01); *A61B 1/00011* (2013.01);
(Continued)

(58) Field of Classification Search
CPC ... A61C 9/0053; A61C 9/0046; A61C 9/0066; A61C 1/088; A61B 1/247; A61B 1/0676;
(Continued)

(56) References Cited

U.S. PATENT DOCUMENTS

| 2,467,432 A | 4/1949 | Kesling et al. |
| 3,407,500 A | 10/1968 | Kesling et al. |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.

(Continued)

*Primary Examiner* — Sang H Nguyen
(74) *Attorney, Agent, or Firm* — Lowenstein Sandler LLP

(57) ABSTRACT

An apparatus is described for determining surface topography of a three-dimensional structure. The apparatus can include a probe and an illumination unit configured to output a plurality of light beams. In many embodiments, the apparatus includes a light focusing assembly. The light focusing assembly can receive and focus each of a plurality of light beams to a respective external focal point. The light focusing assembly can be configured to overlap the plurality of light beams within a focus changing assembly in order to move the external focal points along a direction of propagation of the light beams. The apparatus can include a detector having an array of sensing elements configured to measure a characteristic of each of a plurality of light beams returning from the illuminated spots and a processor coupled to the detector and configured to generate data representative of topography of the structure based on the measured characteristic.

20 Claims, 10 Drawing Sheets

Related U.S. Application Data continuation of application No. 15/220,336, filed on Jul. 26, 2016, now Pat. No. 9,844,427, which is a continuation of application No. 14/323,215, filed on Jul. 3, 2014, now Pat. No. 9,439,568.

(51) Int. Cl.

| | | |
|---|---|---|
| A61B 1/00 | (2006.01) | |
| A61B 1/06 | (2006.01) | |
| A61B 1/247 | (2006.01) | |
| A61C 1/08 | (2006.01) | |
| G01B 11/30 | (2006.01) | |
| G01B 11/24 | (2006.01) | |

(52) U.S. Cl.
CPC ........ *A61B 1/00045* (2013.01); *A61B 1/0676* (2013.01); *A61B 1/247* (2013.01); *A61B 5/0013* (2013.01); *A61B 5/0022* (2013.01); *A61B 5/0088* (2013.01); *A61B 5/7228* (2013.01); *A61C 1/088* (2013.01); *A61C 9/0046* (2013.01); *A61C 9/0053* (2013.01); *G01B 11/24* (2013.01); *G01B 11/30* (2013.01); *A61B 2562/0233* (2013.01)

(58) Field of Classification Search
CPC ............ A61B 1/00009; A61B 1/00011; A61B 1/00045; A61B 5/0088; A61B 5/7228; A61B 5/0013; A61B 5/0022; A61B 2562/0233; G01B 11/30; G01B 11/24
See application file for complete search history.

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,676,671 A | 7/1972 | Edward |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,368,955 A | 1/1983 | Masson |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,588,265 A | 5/1986 | Takahashi |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,783,593 A | 11/1988 | Noble |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,004,328 A * | 4/1991 | Suzuki ................. G02B 3/00 348/E5.027 |
| 5,011,405 A | 4/1991 | Lemchen |
| 5,017,133 A | 5/1991 | Miura et al. |
| 5,027,281 A | 6/1991 | Rekow et al. |
| 5,034,903 A * | 7/1991 | Alfano ............... G01N 23/2254 250/311 |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,132,143 A | 7/1992 | Deckard |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,239,178 A | 8/1993 | Derndinger et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,372,502 A | 12/1994 | Massen et al. |
| 5,378,154 A | 1/1995 | Van Der Zel |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,503,152 A | 4/1996 | Oakley et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,659,420 A | 8/1997 | Wakai et al. |
| 5,668,665 A | 9/1997 | Choate |
| 5,683,243 A | 11/1997 | Andreiko et al. |
| 5,692,894 A | 12/1997 | Schwartz et al. |

(56) References Cited

U.S. PATENT DOCUMENTS

| | | |
|---|---|---|
| 5,725,376 A | 3/1998 | Poirier et al. |
| 5,725,378 A | 3/1998 | Wang et al. |
| 5,733,126 A | 3/1998 | Andersson et al. |
| 5,737,084 A | 4/1998 | Ishihara et al. |
| 5,740,267 A | 4/1998 | Echerer et al. |
| 5,742,700 A | 4/1998 | Yoon et al. |
| 5,790,242 A | 8/1998 | Stern et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,236,521 B1 | 5/2001 | Nanba |
| 6,244,861 B1 | 6/2001 | Andreiko et al. |
| 6,263,234 B1 | 7/2001 | Engelhardt et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |
| 6,399,942 B1 | 6/2002 | Ishihara |
| 6,402,707 B1 | 6/2002 | Ernst et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,573,998 B2 | 6/2003 | Cohen-Sabban et al. |
| 6,594,539 B1 | 7/2003 | Geng |
| 6,629,840 B2 | 10/2003 | Chishti et al. |
| 6,697,164 B1 | 2/2004 | Babayoff et al. |
| 6,705,863 B2 | 3/2004 | Phan et al. |
| 6,722,880 B2 | 4/2004 | Chishti et al. |
| 6,940,611 B2 | 9/2005 | Babayoff et al. |
| 7,092,107 B2 | 8/2006 | Babayoff et al. |
| 7,230,725 B2 | 6/2007 | Babayoff et al. |
| 7,319,529 B2 | 1/2008 | Babayoff |
| 7,446,885 B2 | 11/2008 | Zabolitzky et al. |
| 7,477,402 B2 | 1/2009 | Babayoff et al. |
| 7,511,829 B2 | 3/2009 | Babayoff et al. |
| 7,561,273 B2 | 7/2009 | Stautmeister et al. |
| 7,626,705 B2 | 12/2009 | Altendorf et al. |
| 7,630,089 B2 | 12/2009 | Babayoff et al. |
| 7,672,527 B2 | 3/2010 | Arenberg et al. |
| 7,724,378 B2 | 5/2010 | Babayoff et al. |
| 7,791,810 B2 | 9/2010 | Powell et al. |
| 7,796,277 B2 | 9/2010 | Babayoff et al. |
| 7,944,569 B2 | 5/2011 | Babayoff et al. |
| 7,990,548 B2 | 8/2011 | Babayoff et al. |
| 8,126,025 B2 | 2/2012 | Takeda et al. |
| 8,310,683 B2 | 11/2012 | Babayoff et al. |
| 8,451,456 B2 | 5/2013 | Babayoff |
| 8,488,113 B2 | 7/2013 | Thiel et al. |
| 8,577,212 B2 | 11/2013 | Thiel et al. |
| 8,638,447 B2 | 1/2014 | Babayoff et al. |
| 8,638,448 B2 | 1/2014 | Babayoff et al. |
| 8,675,706 B2 | 3/2014 | Seurin et al. |
| 8,743,923 B2 | 6/2014 | Geske et al. |
| 8,767,270 B2 | 7/2014 | Curry et al. |
| 9,089,277 B2 | 7/2015 | Babayoff et al. |
| 9,261,356 B2 | 2/2016 | Lampert et al. |
| 9,261,358 B2 | 2/2016 | Atiya et al. |
| 9,393,087 B2 | 7/2016 | Moalem |
| 9,439,568 B2 | 9/2016 | Atiya et al. |
| 9,675,429 B2 | 6/2017 | Lampert et al. |
| 9,696,264 B2 | 7/2017 | Lange et al. |
| 9,752,867 B2 | 9/2017 | Atiya et al. |
| 9,844,427 B2 | 12/2017 | Atiya et al. |
| 9,939,258 B2 | 4/2018 | Lampert et al. |
| 10,258,437 B2 | 4/2019 | Atiya et al. |
| 10,260,869 B2 | 4/2019 | Atiya et al. |
| 2002/0006597 A1 | 1/2002 | Andreiko et al. |
| 2002/0023903 A1 | 2/2002 | Ann et al. |
| 2002/0030812 A1 | 3/2002 | Ortyn et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer et al. |
| 2004/0128010 A1 | 7/2004 | Pavlovskaia et al. |
| 2005/0055118 A1 | 3/2005 | Nikolskiy et al. |
| 2005/0283065 A1 | 12/2005 | Babayoff et al. |
| 2006/0158665 A1 | 7/2006 | Babayoff et al. |
| 2007/0109559 A1 | 5/2007 | Babayoff et al. |
| 2007/0114362 A1 | 5/2007 | Feng et al. |
| 2007/0211605 A1 | 9/2007 | Sakamoto |
| 2009/0051995 A1 | 2/2009 | Shechterman |
| 2009/0218514 A1 | 9/2009 | Klunder et al. |
| 2009/0219612 A1 | 9/2009 | Hirata |
| 2010/0099984 A1 | 4/2010 | Graser et al. |
| 2011/0080576 A1 | 4/2011 | Thiel et al. |
| 2012/0081786 A1 | 4/2012 | Mizuyama et al. |
| 2012/0147912 A1 | 6/2012 | Moench et al. |
| 2012/0281293 A1 | 11/2012 | Gronenborn et al. |
| 2013/0100272 A1* | 4/2013 | Price .................. G02B 7/38 348/79 |
| 2013/0163627 A1 | 6/2013 | Seurin et al. |
| 2013/0177866 A1 | 7/2013 | Babayoff et al. |
| 2013/0266326 A1 | 10/2013 | Joseph et al. |
| 2013/0286174 A1 | 10/2013 | Urakabe et al. |
| 2014/0022356 A1 | 1/2014 | Fisker et al. |
| 2014/0104620 A1 | 4/2014 | Babayoff et al. |
| 2014/0139634 A1 | 5/2014 | Lampert et al. |
| 2015/0037750 A1 | 2/2015 | Moalem |
| 2016/0000535 A1 | 1/2016 | Atiya et al. |
| 2016/0003610 A1 | 1/2016 | Lampert et al. |
| 2016/0003613 A1 | 1/2016 | Atiya et al. |
| 2016/0015489 A1 | 1/2016 | Atiya et al. |
| 2016/0064898 A1 | 3/2016 | Atiya et al. |
| 2016/0109226 A1 | 4/2016 | Atiya et al. |
| 2017/0027670 A1 | 2/2017 | Atiya et al. |
| 2017/0328704 A1 | 11/2017 | Atiya et al. |

FOREIGN PATENT DOCUMENTS

| | | |
|---|---|---|
| AU | 5598894 A | 6/1994 |
| CA | 1121955 A | 4/1982 |
| CN | 1646894 A | 7/2005 |
| DE | 2749802 A1 | 5/1978 |
| DE | 69327661 T2 | 7/2000 |
| DE | 102005043627 A1 | 3/2007 |
| DE | 102012009836 A1 | 11/2013 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1780575 A1 | 5/2007 |
| EP | 1970668 A1 | 9/2008 |
| EP | 1970743 A1 | 9/2008 |
| EP | 2213223 A1 | 8/2010 |
| EP | 2439489 A2 | 4/2012 |

(56) References Cited

FOREIGN PATENT DOCUMENTS

| | | |
|---|---|---|
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | 08508174 | 9/1996 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-9924786 A1 | 5/1999 |
| WO | WO-0008415 A1 | 2/2000 |
| WO | WO-02095475 A1 | 11/2002 |
| WO | WO-2007090865 A1 | 8/2007 |
| WO | WO-2012083967 A1 | 6/2012 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Operation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the lnvisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
CEREC Omnicam and CEREC Bluecam brochure. The first choice in every case. The Dental Company Sirona. 2014.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, Part 3 The Computer Gives New Vision—Literally, Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.

(56) References Cited

OTHER PUBLICATIONS

Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
Dummer, et al. Computed Radiography Imaging Based on High-Density 670 nm VCSEL Arrays. Proceedings of SPIE vol. 7557, 75570H (2010)http://vixarinc.com/pdf/SPIE_radiography_manuscript_submission1.pdf.
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
International search report and written opinion dated Oct. 23, 2015 for PCT/IB2015/054911.
"International search report with written opinion dated Oct. 15, 2015 for PCT/IB2015/054910".
Ishii. Fast Focus Mechanism Using a Pair of Convergent and Divergent Lenses Differentially for Three-dimensional Imaging. IEICE Transactions on Information and Systems. Jan. 1, 2012. pp. 168-172.
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).

(56) References Cited

OTHER PUBLICATIONS

Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pellin Broca Prisms—Specifications. Thor Labs. Updated Nov. 30, 2012. www.thorlabs.com.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schaack. Variation of Magnification with Focus. Applied Optics, vol. 41, No. 7. Mar. 1, 2002. p. 1282.
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,<http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.

(56) References Cited

OTHER PUBLICATIONS

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances-Pro Lab product information for patients, 2 pages (2002).

\* cited by examiner

APPARATUS AND METHOD FOR MEASURING SURFACE TOPOGRAPHY OPTICALLY

CROSS-REFERENCE

This application is a continuation of U.S. application Ser. No. 15/811,365, filed Nov. 13, 2017, now U.S. Pat. No. 10,258,437, issued Apr. 16, 2019, which is a continuation of U.S. application Ser. No. 15/220,336, filed Jul. 26, 2016, now U.S. Pat. No. 9,844,427, issued Dec. 19, 2017, which is a continuation of U.S. application Ser. No. 14/323,215, filed Jul. 3, 2014, now U.S. Pat. No. 9,439,568, issued Sep. 13, 2016, each of which are incorporated herein by reference in their entirety.

BACKGROUND

A variety of approaches have been developed for measuring surface topography optically. For example, optical systems and methods have been developed and employed that can be used to optically measure surface topography of a patient's teeth. The measured surface topography of the teeth can be used, for example, to design and manufacture a dental prosthesis and/or to determine an orthodontic treatment plan to correct a malocclusion.

One technique for measuring surface topography optically employs laser triangulation to measure distance between a surface of the tooth and an optical distance probe, which is inserted into the oral cavity of the patient. Surface topography measured via laser triangulation, however, may be less accurate than desired due to, for example, sub-optimal reflectivity from the surface of the tooth.

Other techniques for measuring surface topography optically, which are embodied in CEREC-1 and CEREC-2 systems commercially available from Siemens GmbH or Sirona Dental Systems, utilize the light-section method and phase-shift method, respectively. Both systems employ a specially designed hand-held probe to measure the three-dimensional coordinates of a prepared tooth. Both of these approaches, however, require a specific coating (i.e. measurement powder and white-pigments suspension, respectively) to be deposited to the tooth. The thickness of the coating layer should meet specific, difficult to control requirements, which leads to inaccuracies in the measurement data.

In yet another technique, mapping of teeth surface is based on physical scanning of the surface by a probe and by determining the probe's position, e.g., by optical or other remote sensing means.

U.S. Pat. No. 5,372,502 discloses an optical probe for three-dimensional surveying. Various patterns are projected onto the tooth or teeth to be measured and corresponding plurality of distorted patterns are captured by the optical probe. Each captured pattern provides refinement of the topography.

SUMMARY

Apparatus and methods for optically determining surface topography of three-dimensional structures are provided. In many embodiments, an apparatus for optically determining surface topography includes a light focusing assembly operable to vary focal depth of light beams incident upon the three-dimensional structure (e.g., a patient's dentition) being measured. The light focusing assemblies disclosed herein provide variation of focal depth with minimal or no moving parts, which provides smaller, faster, and more compact optics.

In one aspect, an apparatus is described for determining surface topography of a three-dimensional structure. In many embodiments, the apparatus includes a light focusing assembly. The light focusing assembly can be configured to overlap the light beams within a focus changing assembly in order to move external focal points of the light beams along a direction of propagation of the light beams. Characteristics of light reflected from the measured structure can be measured. The measured characteristics can be used to generate data representative of topography of the structure.

In another aspect, an apparatus is described for determining surface topography of a three-dimensional structure. In many embodiments, the apparatus includes a light focusing assembly. The light focusing assembly can include a convergent lens and a divergent lens. The separation between the convergent lens and divergent lens can be varied in order to displace external focal points of the light beams along a direction of propagation of the light beams. Characteristics of light reflected from the measured structure can be measured. The measured characteristics can be used to generate data representative of topography of the structure.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
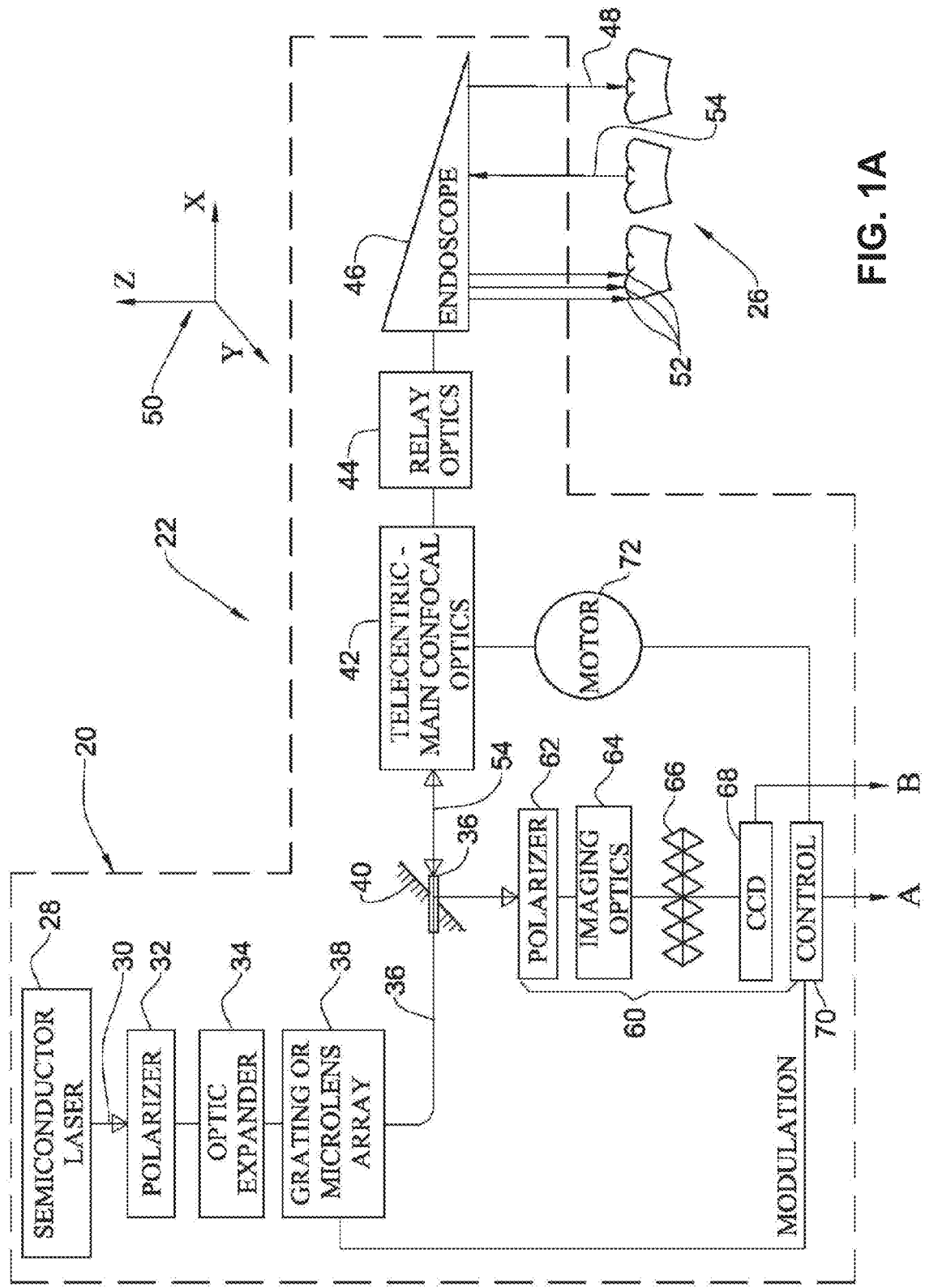
FIGS. 1A and 1B schematically illustrate, by way of a block diagram, an apparatus in accordance with many embodiments (FIG. 1B is a continuation of FIG. 1A)

In many embodiments, an apparatus for optically determining surface topography includes a light focusing assembly that is configured to controllably vary focal depth of light beams that are projected towards a three-dimensional structure (e.g., a patient's dentition) being measured. In contrast to conventional approaches that employ substantial movement of optical components, the light focusing assemblies disclosed herein employ few if any moving parts, thereby being smaller, faster, and more compact. Furthermore, the apparatus and methods disclosed herein for optically determining surface topography can be used to vary the focal depth of the light beams while maintaining telecentricity. Telecentric optics produce constant image magnification independent of the object distance over a defined telecentric range, and can therefore be advantageous for improving the accuracy of optical measurement systems.

The apparatus and methods described herein can be used to take optical measurements of the surfaces of any suitable three-dimensional structure. In many embodiments, optical measurements are taken to generate data representing the three-dimensional surface topography of a patient's dentition. The data can be used, for example, to produce a three-dimensional virtual model of the dentition that can be displayed and manipulated. The three-dimensional virtual models can be used to, for example, define spatial relationships of a patient's dentition that are used to create a dental prosthesis (e.g., a crown or a bridge) for the patient. The surface topography data can be stored and/or transmitted and/or output, such as to a manufacturing device that can be used to, for example, make a physical model of the patient's dentition for use by a dental technician to create a dental prosthesis for the patient.

In one aspect, an apparatus is provided for determining surface topography of a three-dimensional structure. The apparatus can include a probe, such as a probing member sized for insertion into the intraoral cavity. The apparatus can include an illumination unit configured to output a plurality of light beams. The light beams can propagate toward the structure along an optical path through the probe to generate illuminated spots on the structure. The surface of the structure reflects the incident light beams thereby producing a plurality of returning light beams. The apparatus can further include a detector configured to measure a characteristic of each of the plurality of light beams returning from the illuminated spots. Such characteristics can include, for example, intensity, wavelength, polarization, phase shift, interference, and/or dispersion of the returning light beams. Any description herein relating to light intensity can also be applied to other suitable characteristics of light, and vice-versa. The measurements of the characteristic(s) can be used to detect whether the incident light beams are focused on the surface of the structure and thereby determine the distance between the optical probe and the three-dimensional structure.

A processor can be coupled to the detector to generate data representative of the topography of the structure based on measured characteristics of each of a plurality of light beams returning from the illuminated spots. For example, the surface topography of the structure can be determined based on measuring the intensities of the returning light beams. In many embodiments, the apparatus is configured such that the intensity of any particular light beam returning from the structure is maximized when the incident light beam is focused on the surface of the structure, thus relating the magnitude of the intensity signal to the focal depth of the apparatus. Consequently, the relative depth of each point on the surface of the structure can be determined by scanning the light beams through a range of focal depths and identifying the focal depth at which the peak intensity signal is obtained. The surface topography of the structure can thus be determined by repeating this process for each point on the structure.

As another example, the surface topography can be determined by using spatial frequency analysis to identify which regions of the structure are in focus. In many embodiments, focused regions will contain higher spatial frequencies than out of focus regions. Accordingly, a distance between the probe and a specified region on the structure for a particular position and orientation of the probe relative to the structure can be determined by identifying when the spatial frequencies of the region are maximized. This approach can be applied to determine the surface topography of structures having spatial details.

In order to scan the focus the light beams through the range of focal depths, the apparatus can include a light focusing assembly. The light focusing assembly can be configured to focus each of a plurality of the light beams to a respective external focal point. The light beams may emanate from the probe at a location disposed between the respective external focal point and the light focusing assembly. To scan the focus of the light beams through the range of focal depths, the light focusing assembly can also be configured to overlap a plurality of the light beams within a focus changing assembly. The focus changing assembly can be operated to displace the external focal points along a direction of propagation of the light beams.

Many configurations are possible for the light focusing assembly and focus changing assembly. For example, at a least a portion of the focus changing assembly can be located at a back focal length of an objective lens of the light focusing assembly in order to inhibit changes in spacing between external focal points of the plurality of light beams when the external focal points move along the direction of propagation of the light beams. Alternatively or in combination, the focus changing assembly can be located along optical paths of the plurality of light beams such that a majority of the plurality of light beams overlaps with other light beams of the plurality along at least a portion of the focus changing assembly in order to inhibit changes in spacing between external focal points of the plurality of light beams when the external focal points move along the direction of propagation of the light beams. Each of the plurality of light beams may comprise a substantially collimated configuration upon entering the focus changing assembly. The focus changing assembly can similarly adjust each of the plurality of light beams to a convergent configuration, a collimated configuration, or a divergent configuration upon exiting the focus changing assembly in order to move the external focal points along the direction of propagation of the light beams. For instance, the focus changing assembly may move the external focal points at least 10 mm.

In many embodiments, the light focusing assembly includes one or more image space lenses and one or more object space lenses, with the focus changing assembly located along an optical path between the one or more image space lenses and the one or more object space lenses. The one or more object space lenses may comprise a telecentric lens and at least a portion of the focus changing assembly may be located at a back focal length of the telecentric lens. The one or more image space lenses may comprise a focal length and location arranged to overlap and substantially collimate the plurality of light beams passing through the focus changing assembly.

In many embodiments, the focus changing assembly includes a variable optical power element operable to move the external focal points without movement of the variable optical power element. The variable optical power element can be operated at a suitable frequency so as to oscillate separation between the external focal points and the probe by a desired range. For example, the variable optical power element may be operable to oscillate separation between the external focal points and the probe by at least 10 mm at a frequency greater than 10 Hz, or at a frequency from approximately 50 Hz to approximately 100 Hz.

Alternatively or in combination, the focus changing assembly can comprise a focus changing group of lenses in which the separation between lenses is varied to displace the external focal points through the range of focal depths. For example, the focus changing group of lenses can include a divergent lens and a convergent lens, with separation between the divergent lens and convergent lens being varied to displace the external focal points. In many embodiments, a change in separation between the lenses of the focus changing group of lenses results in a change in separation between the external focal points and the probe that is greater than the change in separation between the lenses. For example, the focus changing assembly can move the external focal points over a distance that is at least two times greater than a corresponding distance moved by at least a portion of the focus changing assembly. The change in separation between the lenses of the focus-changing group may result in a change in separation between the external focal points and the probe of at least 5 times or approximately 7.5 times the change in separation between the lenses of the focus changing group of lenses. Additionally, in many embodiments, the variable optical power element or the focus changing group lenses is operable to oscillate separation between the external focal points and the probe by a suitable distance and at a suitable frequency. For instance, the focus changing group of lenses may be operable to oscillate separation between the external focal points and the probe by at least 10 mm at a frequency greater than 10 Hz, or by at least 15 mm at a frequency from approximately 10 Hz to approximately 100 Hz.

In another aspect, a method is provided for determining surface topography of a three-dimensional structure. The method includes generating illuminated spots on the structure using a light focusing assembly to receive and focus each of a plurality of light beams to a respective external focal point external to a probe sized to be inserted into an intraoral cavity of a patient. The light focusing assembly can be operated to overlap each of the plurality of light beams within a focus changing assembly. The focus changing assembly can be operated to displace the external focal points along a direction of propagation of the plurality of light beams. The surface of the structure can reflect the light from the illuminated spots thereby producing a plurality of returning light beams. A characteristic of each of a plurality of light beams returning from the illuminated spots can be measured. Based on the measured characteristics, data representative of topography of the structure can be generated, as previously described herein.

In another aspect, an apparatus is provided for determining surface topography of a three-dimensional structure. The apparatus can include a probe, such as a probing member sized for insertion into the intraoral cavity. The apparatus can include an illumination unit configured to output an array of light beams. The light beams can propagate toward the structure along an optical path through the probe to generate illuminated spots on the structure. The surface of the structure can reflect the light from the illuminated spots thereby producing a plurality of returning light beams. The apparatus can further include a detector configured to measure a characteristic of each of the plurality of light beams returning from the illuminated spots. A processor can be coupled to the detector to generate data representative of the topography of the structure based on measured characteristics of each of a plurality of light beams returning from the illuminated spots, as previously described herein. The characteristic may comprise an intensity, for example.

To scan the focus of the light beams through the range of focal depths, the apparatus can include a light focusing assembly that includes a convergent lens and a divergent lens. The light focusing assembly can be configured to overlap each of the plurality of light beams to a system aperture disposed between the light focusing assembly and a location where the light beams emanate from the probe. The light focusing assembly can be operable to vary separation between the convergent lens and divergent lens to vary separation between the probe and an external focal point for each of the plurality of the light beams. In many embodiments, a change in separation between the convergent lens and the divergent lens results in a change in separation between the external focal points and the probe that is greater than the change in separation between the convergent lens and the divergent lens (e.g., at least 2 times or at least 4 times greater). In many embodiments, the divergent lens is disposed between the convergent lens and the system aperture. The apparatus can further include a telecentric lens disposed on the optical path between the system aperture and the external focal points.

In another aspect, a method is provided for determining surface topography of a three-dimensional structure. The method includes generating an array of light beams that propagate along an optical path to form illuminated spots on the structure. The optical path passes through a convergent lens, a divergent lens, and a probe sized to be inserted into an intraoral cavity of a patient. The divergent lens can be disposed between the convergent lens and a location where the light beams emanate from the probe. The surface of the structure reflects light from the illuminated spots thereby producing a plurality of returning light beams. A characteristic of each of a plurality light beams returning from the structure is measured. Based on the measured characteristic, data representative of topography of the structure is generated, as previously described herein. To scan the focus of the light beams through the range of focal depths, the separation between the convergent lens and the divergent lens is varied to vary separation between the probe and respective external focal points of each of a plurality of the light beams.

Figure 1B:
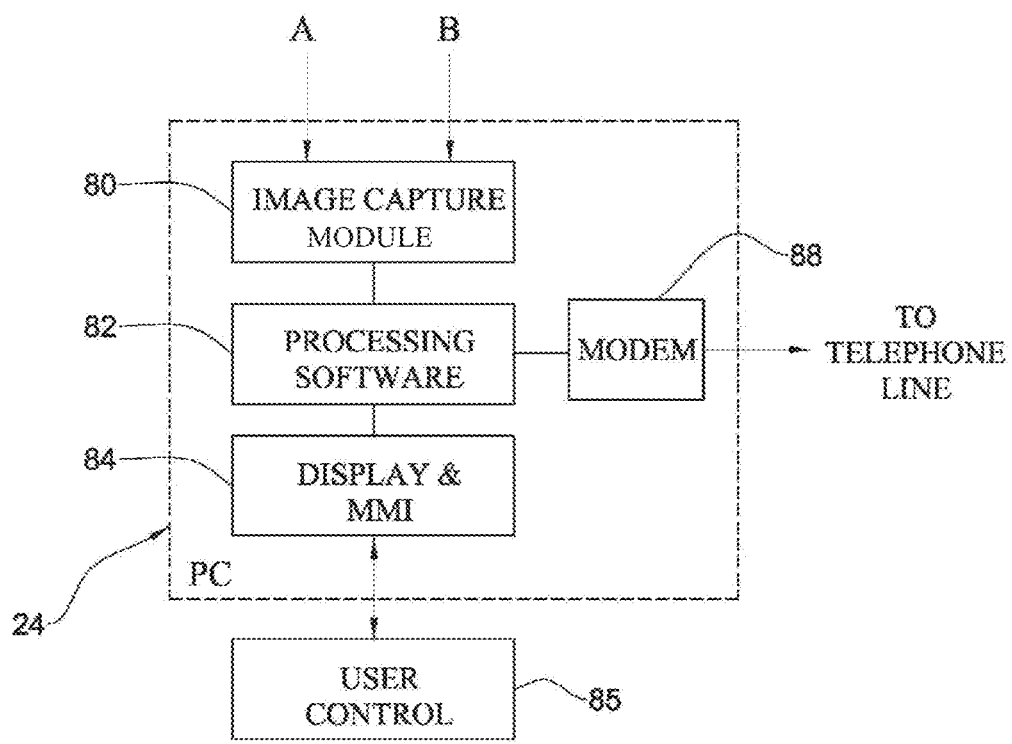

Turning now to the drawings, in which like numbers designate like elements in the various figures, FIGS. 1A and 1B illustrate an apparatus 20 for measuring surface topography optically. The apparatus 20 includes an optical device 22 coupled to a processor 24. The illustrated embodiment is particularly useful for measuring surface topography of a patient's teeth 26. For example, the apparatus 20 can be used to measure surface topography of a portion of the patient's teeth where at least one tooth or portion of tooth is missing to generate surface topography data for subsequent use in design and/or manufacture of a prosthesis for the patient (e.g., a crown or a bridge). It should be noted, however, that the invention is not limited to measuring surface topography of teeth, and applies, mutatis mutandis, also to a variety of other applications of imaging of three-dimensional structure of objects (e.g., for the recordal of archeological objects, for imaging of a three-dimensional structure of any suitable item such as a biological tissue, etc.).

The optical device 22 includes, in the illustrated embodiment, a light source 28 (e.g., a semiconductor laser unit) emitting a light, as represented by arrow 30. The light passes through a polarizer 32, which causes the light passing through the polarizer 32 to have a certain polarization. The light then enters into an optic expander 34, which increases the diameter of the light beam 30. The light beam 30 then passes through a module 38, which can, for example, be a grating or a micro lens array that splits the parent beam 30 into a plurality of light beams 36, represented here, for ease of illustration, by a single line.

The optical device 22 further includes a partially transparent mirror 40 having a small central aperture. The mirror 40 allows transfer of light from the light source 28 through the downstream optics, but reflects light travelling in the opposite direction. It should be noted that in principle, rather than a partially transparent mirror, other optical components with a similar function may be used (e.g., a beam splitter). The aperture in the mirror 40 improves the measurement accuracy of the apparatus. As a result of this mirror structure, the light beams produce a light annulus on the illuminated area of the imaged object as long as the area is not in focus. The annulus becomes a sharply-focused illuminated spot when the light beam is in focus relative to the imaged object. Accordingly, a difference between the measured intensity when out-of-focus and in-focus is larger. Another advantage of a mirror of this kind, as opposed to a beam splitter, is that internal reflections that occur in a beam splitter are avoided, and hence the signal-to-noise ratio is greater.

The optical device 22 further includes confocal optics 42, typically operating in a telecentric mode, relay optics 44, and an endoscopic probe member 46. In many embodiments, the confocal optics 42 is configured to avoid distance-introduced magnification changes and maintain the same magnification of the image over a wide range of distances in the Z direction (the Z direction being the direction of beam propagation). In many embodiments, the confocal optics 42 are telecentric, and can even be double telecentric. Double telecentric confocal optics (telecentric in both image space and object space) can provide improved optical measurement accuracies compared to non-telecentric optics or optics telecentric in image space or object space only. Exemplary embodiments of a light focusing assembly that can be included in the confocal optics 42 are described below. In many embodiments, the relay optics 44 is configured to maintain a certain numerical aperture of the light beam's propagation.

The endoscopic probe member 46 can include a light-transmitting medium, which can be a hollow object defining within it a light transmission path or an object made of a light transmitting material (e.g., a glass body or tube). The light-transmitting medium may be rigid or flexible (e.g., fiber optics). In many embodiments, the endoscopic probe member 46 includes a mirror of the kind ensuring total internal reflection and directing the incident light beams towards the patient's teeth 26. The endoscope 46 thus emits a plurality of incident light beams 48 impinging on to the surface of the patient's teeth 26.

The incident light beams 48 form an array of light beams arranged in an X-Y plane, relative to a Cartesian reference frame 50, and propagating along the Z-axis. When the incident light beams 48 are incident upon an uneven surface, resulting illuminated spots 52 are displaced from one another along the Z-axis, at different $(X_i,Y_i)$ locations. Thus, while an illuminated spot 52 at one location may be in focus for a given focal length produced by the confocal optics 42, illuminated spots 52 at other locations may be out-of-focus. Therefore, the light intensity of the returned light beams of the focused spots will be at its peak, while the light intensity at other spots will be off peak. Thus, for each illuminated spot, a plurality of measurements of light intensity are made at different positions along the Z-axis and for each of such $(X_i,Y_i)$ locations, typically the derivative of the intensity over distance (Z) will be made, and the $Z_i$ distance yielding the maximum derivative, $Z_0$, will be the in-focus distance. As pointed out above, where, as a result of use of the punctured mirror 40, the incident light forms a light disk on the surface when out of focus and a sharply-focused light spot only when in focus, the distance derivative will be larger when approaching in-focus position thus increasing accuracy of the measurement.

The light reflected from each of the illuminated spots 52 includes a beam travelling initially in the Z axis in the opposite direction of the optical path traveled by the incident light beams. Each returned light beam 54 corresponds to one of the incident light beams 36. Given the asymmetrical properties of mirror 40, the returned light beams 54 are reflected in the direction of a detection assembly 60. The detection assembly 60 includes a polarizer 62 that has a plane of preferred polarization oriented normal to the polarization plane of polarizer 32. The returned polarized light beam 54 pass through imaging optics 64, typically a lens or a plurality of lenses, and then through an array of pinholes 66. Each returned light beam 54 passes at least partially through a respective pinhole of the array of pinholes 66. A sensor array 68, which can be a charge-coupled device (CCD) or any other suitable image sensor, includes a matrix of sensing elements. In many embodiments, each sensing element represents a pixel of the image and each sensing element corresponds to one pinhole in the array 66.

The sensor array 68 is connected to an image-capturing module 80 of the processor unit 24. The light intensity measured by each of the sensing elements of the sensor array 68 is analyzed, in a manner described below, by the processor 24. Although the optical device 22 is depicted in FIGS. 1A and 1B as measuring light intensity, the device 22 can also be configured to measure other suitable characteristics (e.g., wavelength, polarization, phase shift, interference, dispersion), as previously described herein.

The optical device 22 includes a control module 70 that controls operation of the light source 28 and/or a motor 72. In many embodiments, the motor 72 is drivingly coupled with the confocal optics 42 so as to scan the focus of the light beams through a range of focal depths along the Z-axis. In a single sequence of operation, the control unit 70 induces motor 72 to reconfigure the confocal optics 42 to change the focal plane location and then, after receipt of a feedback signal that the location has changed, the control module 70 induces the light source 28 to generate a light pulse. The control module 70 synchronizes the operation of the image-capturing module 80 with the operation of the confocal optics 42 and the light source 28 during acquisition of data representative of the light intensity (or other characteristic) from each of the sensing elements. Then, in subsequent sequences, the confocal optics 42 causes the focal plane to change in the same manner and intensity data acquisition continues over a range of focal lengths.

The intensity data is processed by the processor 24 per processing software 82 to determine relative intensity in each pixel over the entire range of focal planes of confocal optics 42. As explained above, once a certain light spot is in focus on the three-dimensional structure being measured, the measured intensity of the returning light beam will be maximal. Thus, by determining the $Z_i$ corresponding to the maximal light intensity or by determining the minimum derivative of the light intensity, for each pixel, the relative in-focus focal length along the Z-axis can be determined for each light beam. Thus, data representative of the three-dimensional topography of the external surfaces of the teeth is obtained. A resulting three-dimensional representation can be displayed on a display 84 and manipulated for viewing (e.g., viewing from different angles, zooming-in or out) by a user control module 85 (e.g., utilizing a computer keyboard, mouse, joystick, or touchscreen). In addition, the data representative of the surface topography can be transmitted through an appropriate data port such as, for example, a modem 88 or any suitable communication network (e.g., a telephone network) to a recipient (e.g., to an off-site CAD/CAM apparatus).

By capturing, in this manner, relative distance data between the probe and the structure being measured from two or more angular locations around the structure (e.g., in the case of a teeth segment, from the buccal direction, lingual direction and/or optionally from above the teeth), an accurate three-dimensional representation of the structure can be generated. The three-dimensional data and/or the resulting three-dimensional representation can be used to create a virtual model of the three-dimensional structure in a computerized environment and/or a physical model fabricated in any suitable fashion (e.g., via a computer controlled milling machine, a rapid prototyping apparatus such as a stereolithography apparatus).

As already pointed out above, a particular and preferred application is imaging of a segment of teeth having at least one missing tooth or a portion of a tooth. The resulting three-dimensional surface topography data can, for example, be used for the design and subsequent manufacture of a crown or any other prosthesis to be fitted into this segment.

Figure 2A:
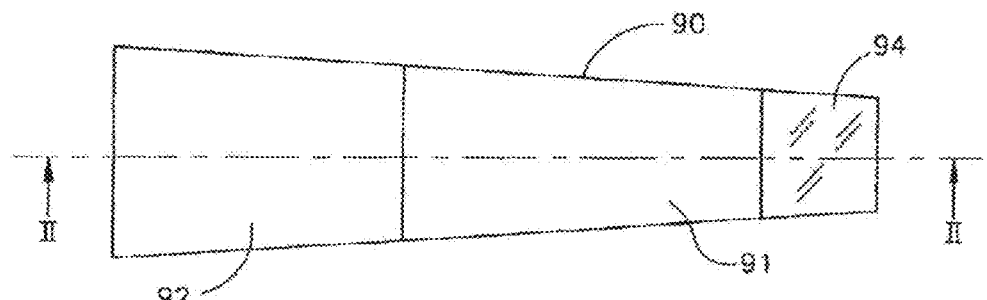
FIG. 2A is a top view of a probing member, in accordance with many embodiments.
Figure 2B:
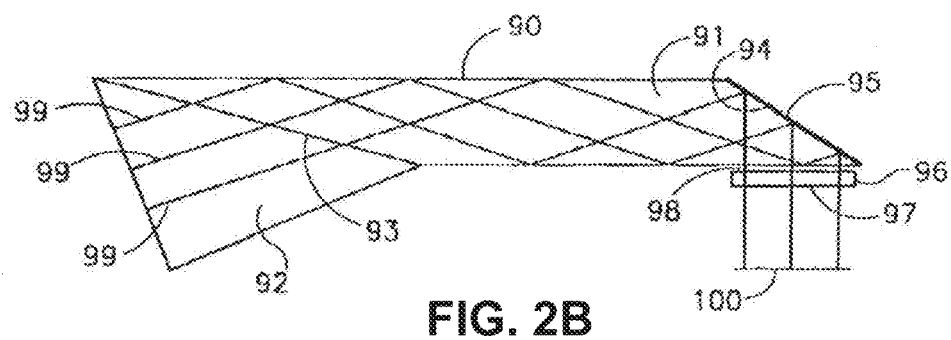
FIG. 2B is a longitudinal cross-section through line II-II in FIG. 2A, depicting exemplary rays passing therethrough.

Referring now to FIGS. 2A and 2B, a probing member 90 is illustrated in accordance with many embodiments. In many embodiments, the probing member 90 forms at least a portion of the endoscope 46. The probing member 90 may be sized to be at least partially inserted into a patient's intraoral cavity. The probing member 90 can be made of a light transmissive material (e.g., glass, crystal, plastic, etc.) and includes a distal segment 91 and a proximal segment 92, tightly glued together in an optically transmissive manner at 93. A slanted face 94 is covered by a reflective mirror layer 95. A transparent disk 96 (e.g., made of glass, crystal, plastic, or any other suitable transparent material) defining a sensing surface 97 is disposed along the optical path distal to the mirror layer 95 so as to leave an air gap 98 between the transparent disk 96 and the distal segment 91. The transparent disk 96 is fixed in position by a holding structure (not shown). Three light rays 99 are represented schematically. As can be seen, the light rays 99 reflect from the walls of the probing member 90 at an angle in which the walls are totally reflective, reflect from the mirror layer 95, and then propagate through the sensing face 97. The light rays 99 are focused on a focusing plane 100, the position of which can be changed by the confocal optics 42.

In many embodiments, the confocal optics 42 includes a telescopic light focusing assembly. The telescopic light focusing assembly is configured and operable to scan the focal points of the light beams through a range of focal depths. Scanning the focal points through a range of focal depths is accomplished in order to determine the in-focus distance for each of the light beams relative to the surface being measured, as previously described herein.

Figure 3:
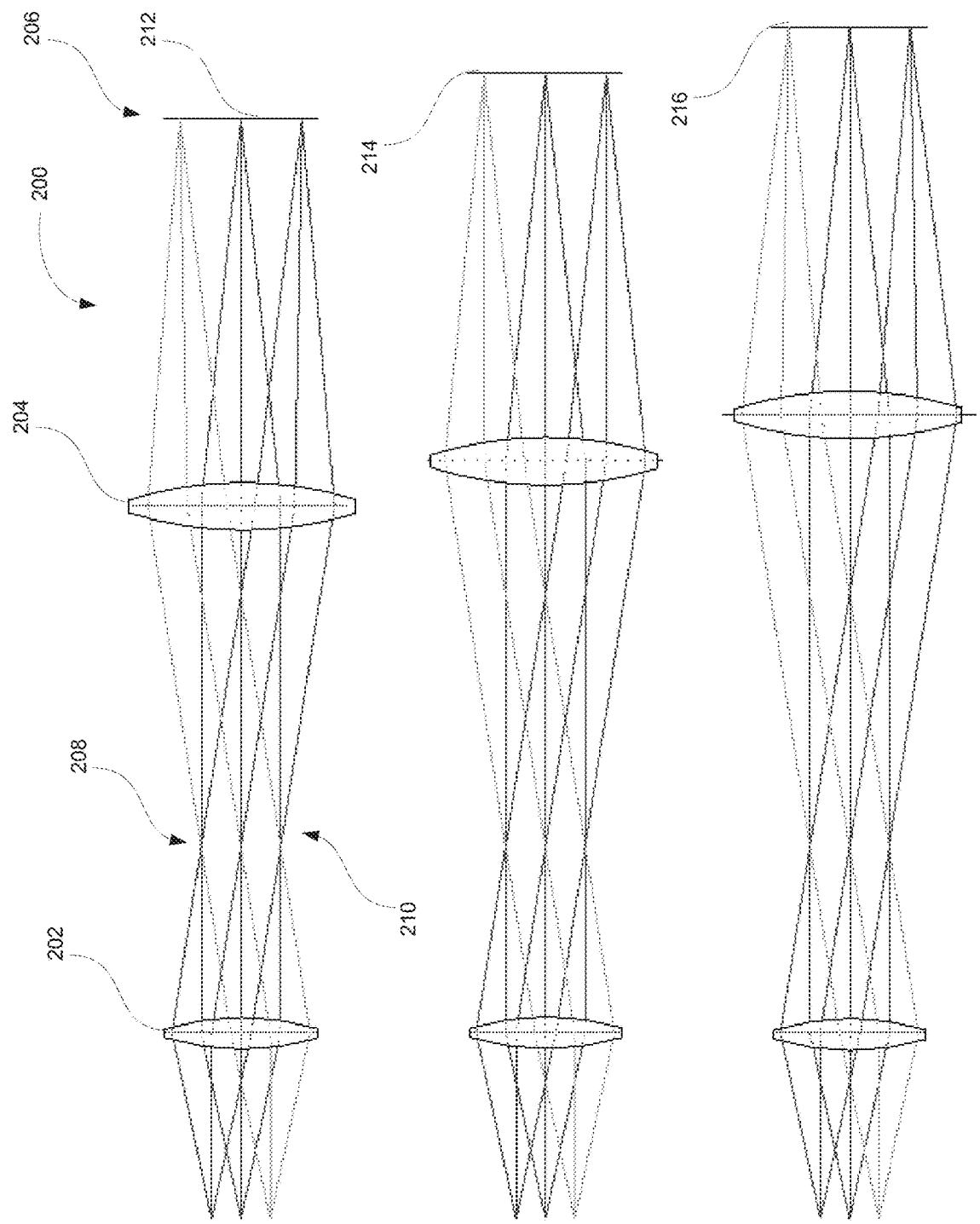
FIG. 3 illustrates a telescopic light focusing assembly, in accordance with many embodiments.

FIG. 3 illustrates a telescopic light focusing assembly 200, in accordance with many embodiments, that can be included in the confocal optics 42. The light focusing assembly 200 is configured and operable to scan the focal points of a plurality of light beams (e.g., a two-dimensional array of light beams) through a range of focal depths. The light focusing assembly 200 can include an image space lens group 202 and an object space lens group 204. The light focusing assembly 200 can be configured and operable to focus the light beams on to an external focal plane 206 (e.g., external to the endoscopic probe member 46) and controllably scan the location of the external focal plane 206 relative to the endoscopic probe member 46. The light beam chief rays may cross the optical axis at the back focal plane of the object space group 204 that is disposed between the image space group 202 and the object space group 204. A system aperture 208 may be situated at or near the back focal plane. An aperture stop (APS) 210 may be positioned at or near the system aperture 208. In many embodiments, the aperture stop 210 includes a circular opening in a physical light blocking plane and is used to define the beam width and, hence, the Numerical Aperture (NA) of the optical system.

Each of the image space lens group 202 and object space lens group 204 can each include one or more lenses. For example, in many embodiments, each of the image space lens group 202 and object space lens group 204 have a single convergent lens (e.g., a biconvex lens). "Lens" may be used herein to refer an element having a single lens or multiple lenses (e.g., doublet or triplet lenses).

To change the relative distance between the endoscopic probe member 46 and the external focal plane 206, the distance between the object space lens group 204 and the image space lens group 202 can be changed, for example, by a mechanism driven by the motor 72. The mechanism may displace one or more of the object space lens group 204 or image space lens group 202 along the direction of beam propagation along the optical axis of the optical system, also called the symmetry axis. By changing the distance between the object space lens group 204 and the image space lens group 202, the external focal plane 206 is displaced along the direction of beam propagation. The external focal plane 206 can be displaced to any suitable position, such as to a near focus position 212, an intermediate focus position 214, or a far focus position 216, by moving the object space lens group 204 along the symmetry axis.

In a telescopic light focusing assembly, telecentricity may be compromised when the external focal plane 206 is displaced due to displacement of the object space lens group 204 relative to the APS 210. The displacement of the object space lens group 204 relative to the APS 210 results in the light rays being refracted by different portions of the object space lens group 204.

Figure 4:
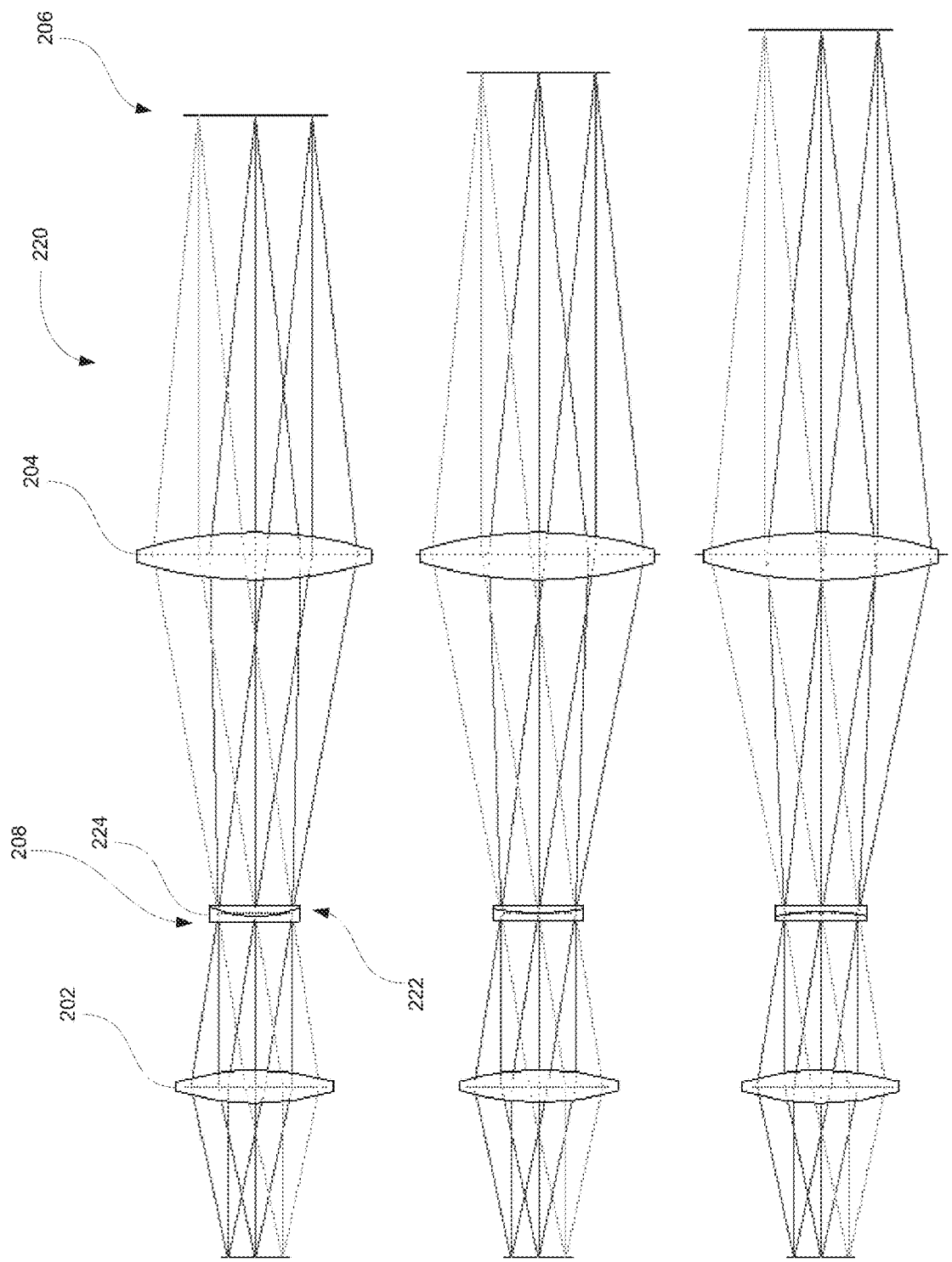
FIG. 4 illustrates a light focusing assembly with a variable optical power element, in accordance with many embodiments.

FIG. 4 illustrates a light focusing assembly 220, in accordance with many embodiments, that can be included in the confocal optics 42. The light focusing assembly 220 can include an image space lens group 202, an object space lens group 204, and a focus changing assembly 222 disposed along an optical path between the image and object space lens groups, such as at or near a system aperture 208. At least one lens element of the image space lens group 202 or object space lens group 204 may be a telecentric lens. One or more optical components of the light focusing assembly 220 can be configured to overlap the plurality of light beams within the focus changing assembly 222. For instance, at least one lens element of the image space lens group 202 may comprise a focal length and location arranged to overlap and substantially collimate the light beams passing through the focus changing assembly 222.

The light focusing assembly 220 can be operable to displace the external focal plane 206 without moving the object space lens group 204 relative to the image space lens group 202. The external focal plane 206 can be displaced along the symmetry axis (e.g., to near, intermediate, and far focus positions) by varying the optical power of the focus changing assembly 222. Accordingly, the light focusing assembly 220 can maintain telecentricity and magnification even when shifting the location of the external focal plane 206. In many embodiments, the positioning and configuration of the focus changing assembly inhibits changes in spacing between external focal points of the external light beams when the external focal points are moved along the direction of propagation of the light beams. For example, the focus changing assembly 222 can be located at or near a back focal length of an objective lens (e.g., object space lens group 204) of the light focusing assembly 220. Alternatively or in combination, the focus changing assembly 222 can be located along the optical paths of the plurality of light beams such that a majority of the plurality of light beams overlap other light beams of the plurality along at least a portion of the focus changing assembly 222. Each of the plurality of light beams may comprise a substantially collimated configuration upon entering the focus changing assembly 222. The focus changing assembly 222 may similarly adjust each of the plurality of light beams to a convergent configuration, a substantially collimated configuration, or a divergent configuration upon exiting the focus changing assembly 222.

In the embodiment illustrated in FIG. 4, the focus changing assembly 220 includes a variable optical power element 224. The variable optical power element 224 can be any suitable optical element having a controllably variable optical power. For example, the variable optical power element 224 can include a variable power lens element or a liquid lens element, such as a liquid lens providing close focus ability and lower power consumption. The liquid lens may be electrically tunable to change the optical power, such as by applying a suitable current (e.g., within a range from 0 mA to 300 mA). In many embodiments, the variable optical power element 224 includes a high refractive index material and a low refractive index material, and an interface between the materials (e.g., a meniscus) may be varied to adjust the optical power. The optical power of the variable optical power element 224 can be varied by any suitable amount, such as by approximately 2 diopters, 5 diopters, 10 diopters, 15 diopters, 20 diopters, or 30 diopters. The optical power of the optical power element 224 can be varied over any suitable range, such as a range between any two of the following: 5 diopters, 8 diopters, 10 diopters, 15 diopters, 16.5 diopters, 20 diopters, 22 diopters, 25 diopters, or 50 diopters. The variable optical power element 224 can be operable to move the external focal plane 206 without movement of the variable optical power element 224 (e.g., without movement along the symmetry axis and/or without movement relative to the other components of the light focusing assembly 220). Accordingly, the light focusing assembly 220 can provide scanning of the external focal plane 206 without any moving optical parts.

Figure 5:
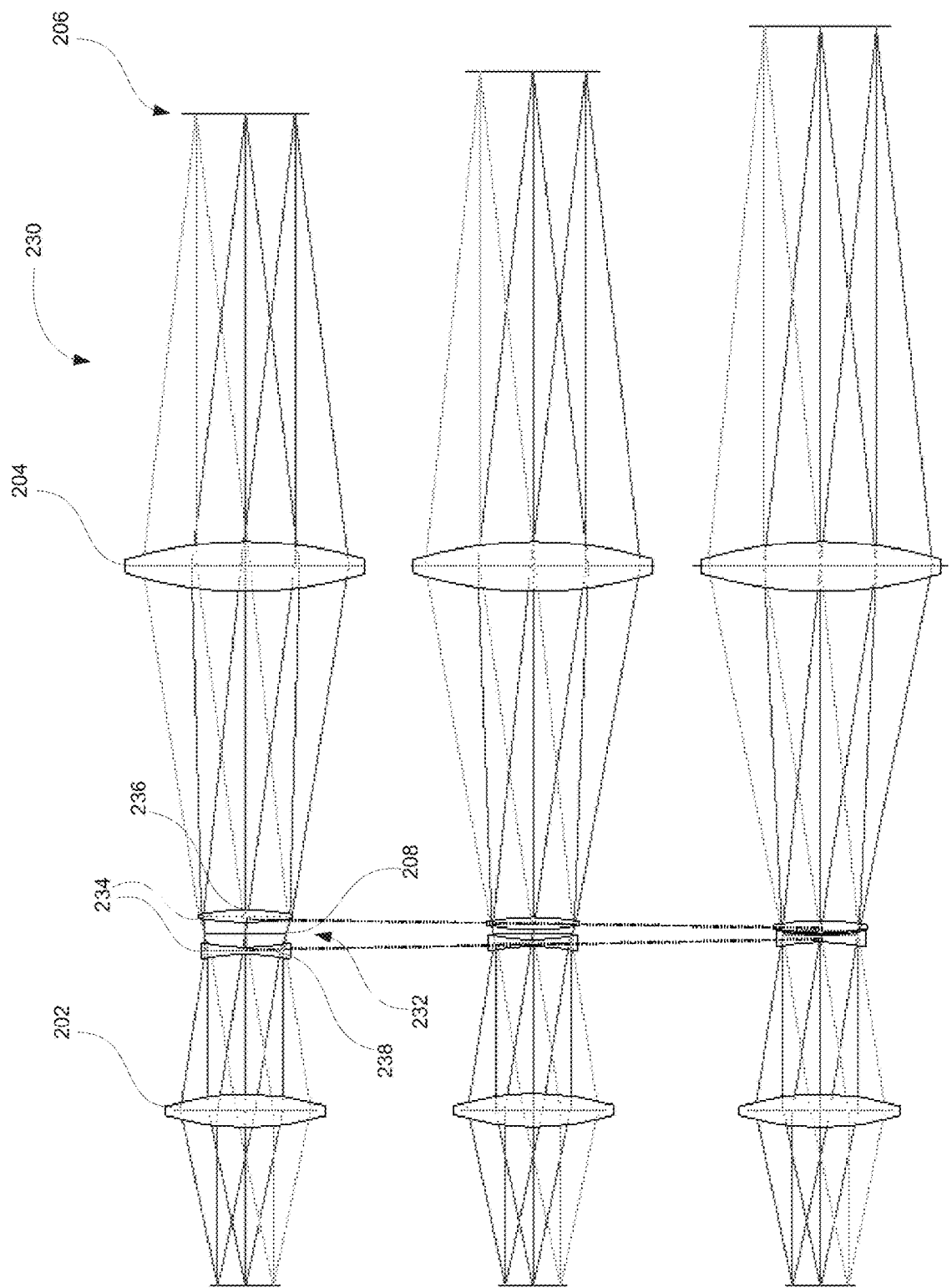
FIG. 5 illustrates a light focusing assembly with a focus changing lens group, in accordance with many embodiments.

FIG. 5 illustrates another light focusing assembly 230, in accordance with many embodiments, that can be included in the confocal optics 42. Similar to the light focusing assembly 220 illustrated in FIG. 4, the light focusing assembly 230 includes an image space lens group 202, an object space lens group 204, and a focus changing assembly 232, which may be disposed at a system aperture 208. The light focusing assembly 230 may receive a plurality of light beams and overlap the light beams within the focus changing assembly 232, as described above. In the light focusing assembly 230, however, the focus changing assembly 232 includes a focus changing lens group 234 instead of a variable optical power element. The optical power of the focus changing lens group 234 can be varied by relative movement between lens elements of the focus changing lens group 234. The relative movement between lens elements of the focus changing lens group 234 can include displacing any suitable component of the focus changing group, such as a single lens element, multiple lens elements, one or more portions of a lens element, one or more portions of multiple lens elements, or any suitable combination. For example, the focus changing group can be a pair of lenses and the movement can be a change in separation between the lenses (e.g., along the symmetry axis). By varying the optical power of the focus changing lens group 234, the external focal plane 206 is displaced along the symmetry axis (e.g., to near, intermediate, and far focus positions).

In the embodiment illustrated in FIG. 5, the focus changing lens group 234 includes a convergent lens 236 (e.g., a biconvex lens) and a divergent lens 238 (e.g., a biconcave lens). The optical power of the focus changing lens group 234 can be changed by varying the separation between the convergent lens 236 and the divergent lens 238. While the focus changing lens group 234 is illustrated as having one convergent lens and one divergent lens, a suitable focus changing lens group can include any suitable combination of lens elements in which relative movement between the lens elements effects a change in optical power.

In many embodiments, the movement of lens elements of the focus changing lens group 234 is small relative to the resulting displacement of the external focal plane 206. For example, an approximately 0 mm to approximately 2 mm movement of the focusing changing lens group 234 may produce an approximately 15 mm movement of the external focal plane 206. The light focusing assembly 230 can be configured such that a change in separation between lens elements of the focus changing lens group 234 results in at least a 2-, 3-, 4-, 5-, 7.5-, or 10-fold larger change in separation between the external focal plane 206 and the endoscopic probe member 46. In many embodiments, the displacement of the external focal plane 206 is approximately 2, 3, 4, 5, 7.5, or 10 times larger than the corresponding change in separation between lens elements of the focus changing lens group 234. The ratio of the movement distance of the external focal plane to the corresponding movement distance of the elements of the focusing changing assembly may be referred to herein as the "movement gain factor." The movement gain factor provided by the focus changing assemblies may be approximately 1, 1.1, 2, 3, 4, 5, 7.5, 10, or 15.

Figure 6:
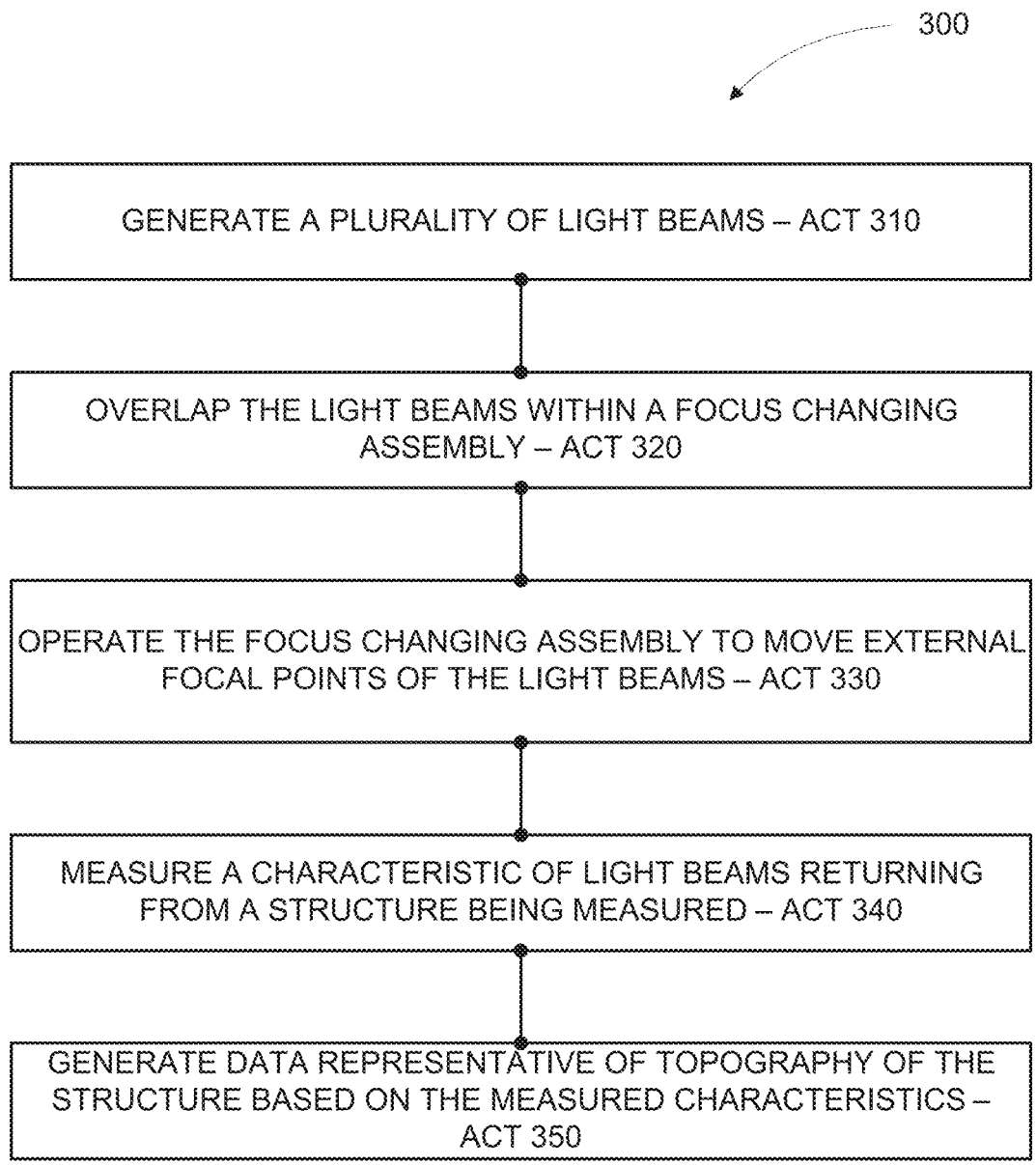
FIG. 6 is a simplified block diagram presenting acts of a method for determining surface topography of a three-dimensional structure, in accordance with many embodiments.

FIG. 6 is a simplified block diagram of acts of a method 300 for determining surface topography of a three-dimensional structure. Any suitable optical assemblies, devices, apparatus, and/or systems, such as suitable embodiments described herein, can be used to practice the method 300.

In act 310, a plurality of light beams is generated. Any suitable device can be used to produce the light beams. For example, referring to FIG. 1A, the apparatus 20 can be used to produce the light beams. The apparatus 20 can include the grating or micro lens array 38, which splits the laser beam 30 emitted by light source 28 into an array of beams 36.

In act 320, the light beams are overlapped within a focus changing assembly. For example, as with the light focusing assembly 220 and with the light focusing assembly 230, the image space lens group 202 can overlap the light beams onto the focus changing assembly 222 and 232, respectively. The focus changing assembly may be disposed at or near a system aperture. Alternatively or in combination, the focus changing assembly may be situated at a back focal length of an objective lens or object space lens group (e.g., a telecentric lens).

In act 330, the focus changing assembly is operated to move the respective external focal points of the light beams. In many embodiments, the focus changing assembly includes a focus changing lens group or a variable optical power element disposed at a system aperture, for example, as in the light focusing assembly 220 or the light focusing assembly 230, respectively. In many embodiments, the external focal points form an external focal plane that can be displaced by varying the optical power of the focus changing assembly. Referring to the endoscopic probe member 46 illustrated in FIG. 2B, in many embodiments, the light beams propagate along an optical path through the endoscopic probe member 46 such that the external focal plane is disposed exterior to the probe (e.g., focusing plane 100). The light beams emanate from the endoscopic probe member 46 at a location disposed between the external focal plane and the light focusing assembly (e.g., sensing face 97). The optical path can be configured to generate an array of illuminated spots on a structure being measured, as illustrated in FIG. 1A by the illuminated spots 52 on the patient's teeth 26.

The external focal points can be displaced to scan the external focal plane through a plurality of focal depths. In many embodiments, the focus changing assembly can be operated to vary the separation distance between the external focal points and the endoscopic probe member 46, such as by oscillating the separation distance through a specified range. For example, the separation distance between the external focal points and the endoscopic probe member 46 can be oscillated by at least 5 mm, at least 10 mm, at least 15 mm, or at least 20 mm. In many embodiments, the oscillation of the separation distance can be within a range of approximately 10 mm to approximately 15 mm. Any suitable oscillation frequency can be used, such as a frequency greater than or equal to approximately 1 Hz, 10 Hz, 20 Hz, 50 Hz, 75 Hz, or 100 Hz. The oscillation frequency may be within a range from approximately 10 Hz to approximately 100 z, or approximately 50 Hz to approximately 100 Hz. In embodiments that employ a focus changing assembly, such as in the light focusing assembly 220 and in the light focusing assembly 230, increased oscillation rates may be achievable relative to the light focusing assembly 200 as a result of the reduced or eliminated movement of light focusing assembly components necessary to displace the external focal plane 206 through the desired distance.

In act 340, the characteristics of a plurality of light beams returning from the structure are measured. For example, as illustrated in FIG. 1A, the returning light beams 54 are reflected by the surface of the structure and each correspond to one of the incident light beams 36 produced by the optical device 22. Any suitable device can be used to measure the characteristics of the returning light beams, such as the sensor array 68. In many embodiments, the measured characteristic is intensity.

In act 350, data representative of topography of the structure is generated based on the measured characteristics, as previously described herein. Any suitable device can be used to receive and generate the data, such as the processor 24 depicted in FIG. 1B.

Table 1 provides an example configuration and operational parameters for the light focusing assembly 200 (hereinafter "telescopic assembly") illustrated in FIG. 3, the light focusing assembly 220 (hereinafter "variable element assembly") illustrated in FIG. 4, and the light focusing assembly 230 (hereinafter "moving lens assembly") illustrated in FIG. 5.

TABLE 1

Example configuration and operational parameters for light focusing assemblies.

| | Telescopic Assembly | Variable Element Assembly | Moving Lens Assembly |
|---|---|---|---|
| External focal plane movement distance | 15 mm | 15 mm | 15 mm |
| Focusing lens movement distance | 15 mm | 0 | 2 mm |
| Optical power change (diopter) | N/A | 5 | N/A |
| Typical moving lens weight | 50 grams | N/A | 5 grams |
| Movement gain factor | 1 | N/A | 7.5 |
| Maximum oscillation frequency | 1 Hz | 100 Hz | 20 Hz |

For each of the three systems in Table 1, the external focal plane is displaced by 15 mm. In the telescopic assembly, a 15 mm movement of an object space lens group weighing 50 g can be used to produce a 15 mm displacement of the external focal plane, for a movement gain factor of 1. The object space lens group can be oscillated at a maximum frequency of approximately 1 Hz. In the variable element assembly, a 5 diopter change in the optical power of a variable optical power lens element without movement of any optical elements can be used to produce a 15 mm displacement of the external focal plane. The optical power of the variable optical power element can be oscillated at maximum frequency of approximately 100 Hz. In the moving lens assembly, a 2 mm movement of a focus changing lens group moving lens that weighs 5 g can be used to produce a 15 mm displacement of the external focal plane, for a movement gain factor of 7.5. The focus changing lens group can be oscillated at a maximum rate of approximately 20 Hz.

Notably, the variable element assembly and the moving lens assembly provide several advantages. With the variable element assembly and the moving lens assembly, the external focal plane may be displaceable with significantly smaller or no movement of optical focusing elements, respectively, when compared to the telescopic assembly. For the moving lens assembly, the weight of the moving optical element may be substantially reduced compared to that of the telescopic assembly, thus reducing the amount of power needed to move the element. Furthermore, the maximum frequency of focal depth oscillation may be significantly higher for the variable element assembly and the moving lens assembly, thereby being compatible for use in systems with increased scanning rate, as compared to the telescopic assembly.

Figure 7:
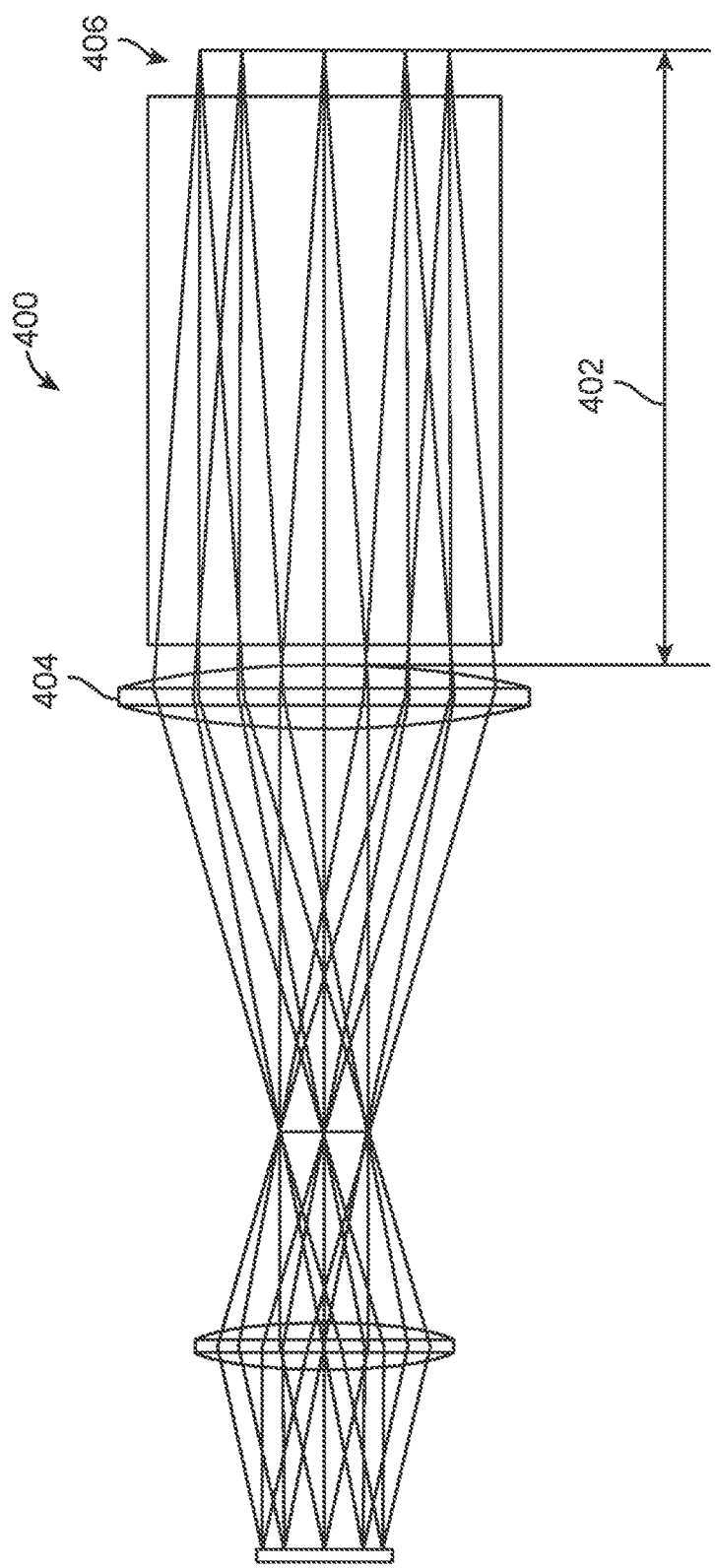
FIG. 7 illustrates a telescopic light focusing assembly, in accordance with many embodiments.

FIG. 7 illustrates an embodiment of a telescopic light focusing assembly 400 similar to the telescopic light focusing assembly 200 illustrated in FIG. 3. In many embodiments, however, the telescopic light focusing assembly 400 may have a significant minimum unfold reach 402 (e.g., 80 mm), which is the minimum distance between the front of the object space lens group 404 and the external focal plane 406. The unfold reach 402 may add to the overall length of the optical path between the grating or microlens array 38 and the structure being measured. It may, however, be advantageous to reduce the length of the optical path between the grating or microlens array 38 and the structure being measured to provide a more compact optical device 22.

Figure 8:
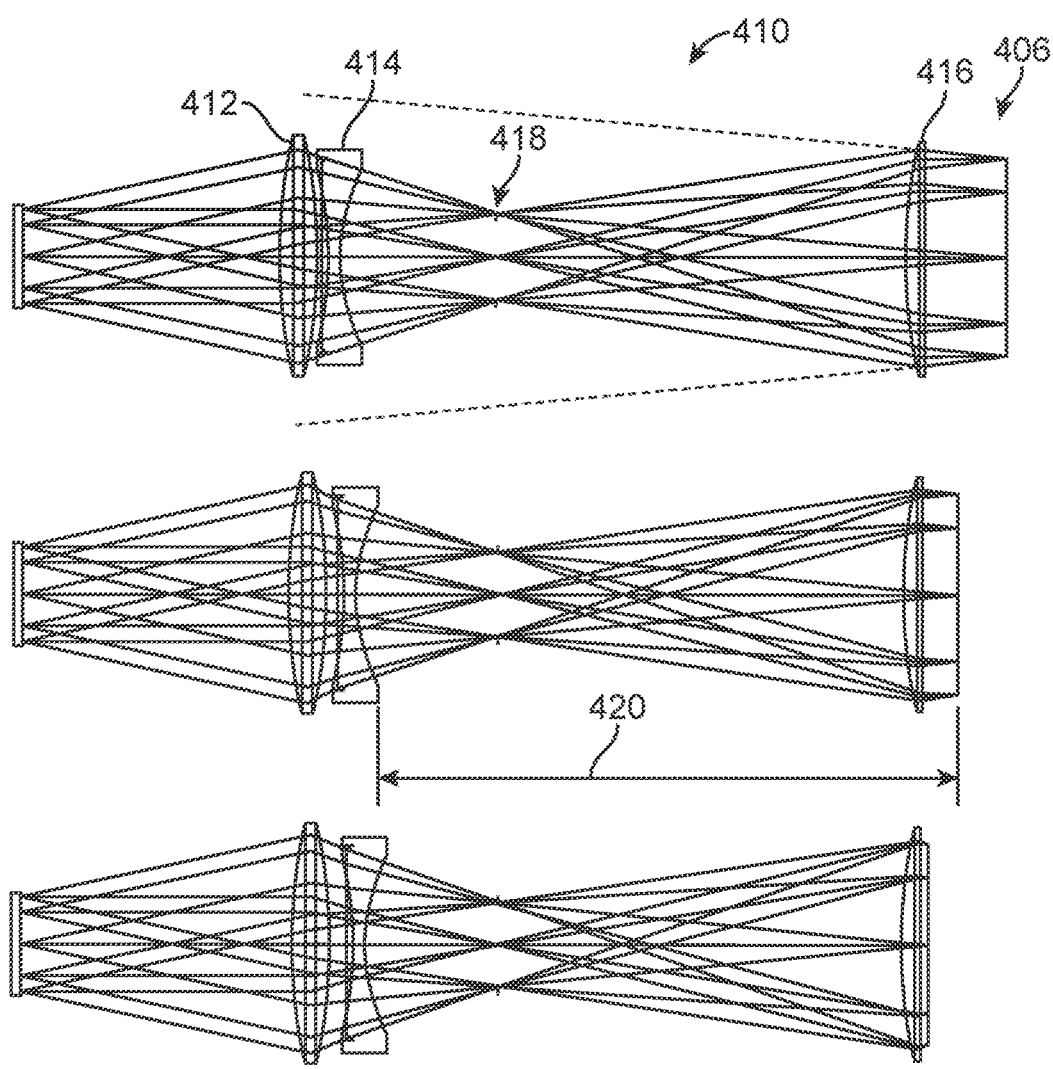
FIG. 8 illustrates a compact light focusing assembly, in accordance with many embodiments.

FIG. 8 illustrates an embodiment of a compact light focusing assembly 410, in accordance with many embodiments. The compact light focusing assembly 410 can include a Z1 lens group 412 and a Z2 lens group 414. A front end lens group 416 can be disposed along the optical path distal to the compact light focusing assembly 410. The Z1 lens group 412 and the Z2 lens group 414 can be adjacently disposed. The Z2 lens group 414 can be disposed between the Z1 lens group 412 and a system aperture 418. The system aperture 418 can be disposed between the Z2 lens group 414 and the front end lens group 416, such as at a back focal length of the front end lens group 416. The Z1 and Z2 lens groups 412, 414 may be configured to overlap a plurality of light beams toward the system aperture 418. The Z1 and Z2 lens groups 412, 414 may adjust the configuration of light beams passing through the system aperture 418, such as by converging, diverging, or substantially collimating the light beams.

The Z1 lens group 412 and the Z2 lens group 414 can include any suitable lens or combination of lenses. For example, the Z1 lens group 412 can include a convergent lens (e.g., a biconvex lens) and the Z2 lens group 414 can include a divergent lens (e.g., a biconvex lens). The front end lens group 416 can include any suitable lens or combination of lenses, such as a convergent lens (e.g., a plano-convex lens with the planar face disposed towards the external focal plane 406). One or more of the Z1 lens group 412, Z2 lens group 414, or front end lens group 416 may include a telecentric lens. For example, in many embodiments, the front end lens group 416 is a telecentric lens. In the illustrated embodiment, an unfolded reach 420 (e.g., 110 mm in the intermediate focus position) between the distal face of the Z2 lens group 414 and the external focal plane 416 results in a reduced optical path length between the grating or microlens array 38 and the structure being measured. In both the telescopic light focusing assembly 400 and the compact light focusing assembly 410, the unfold reach can be measured from the distal face of a lens group that is moved so as to displace the location of the external focal plane 406.

In the compact light focusing assembly 410, the external focal plane 406 can be displaced along the symmetry axis by varying the separation between the Z1 lens group 412 and the Z2 lens group 414. Varying the separation between the Z1 lens group 412 and the Z2 lens group 414 can be accomplished by moving the Z1 lens group 412, moving the Z2 lens group 414, or moving both the Z1 lens group 412 and the 9Z2 lens group 414. For example, the separation between a convergent and divergent lens can be increased to vary the external focal plane between far, intermediate, and near focus positions.

Figure 9:
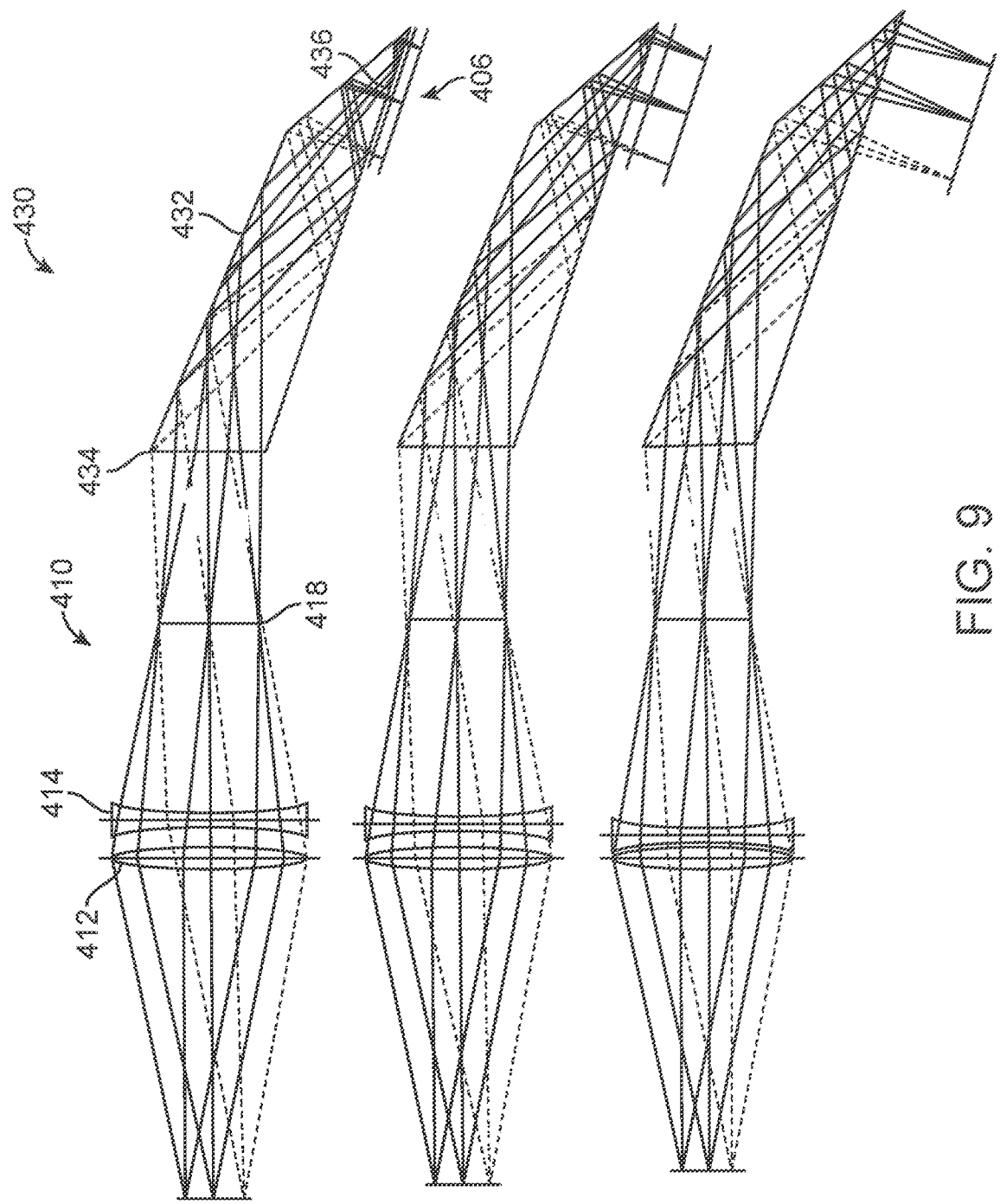
FIG. 9 illustrates a compact light focusing assembly and an optical probe, in accordance with many embodiments.

FIG. 9 illustrates an optical assembly 430 that includes the compact light focusing assembly 410 and a probe 432 in accordance with many embodiments. The light beams focused by the compact light focusing assembly 410 can enter the probe 432 through a face 434 disposed towards the system aperture 418, reflect off the walls of the probe, and emanate from a face 436 disposed towards the external focal plane 406. The probe 432 can be manufactured from any suitable material, such as a light transmissive material (e.g., glass). In many embodiments, the walls of the probe are totally reflective, such that light beams reflect off the internal walls of the probe as they propagate through the probe. The probe can be probing member 90, as illustrated in FIGS. 2A and 2B. In many embodiments, a thin lens is positioned at a probe exit aperture 436.

The external focal plane 406 can be displaced relative to the probe 432 along the direction of the light beams emanating from the probe. The external focal plane 406 can be displaced by varying the separation between the Z1 lens group 412 and the Z2 lens group 414, as described above.

In many embodiments, a change in the distance between the Z1 and Z2 lens groups produces a larger change in the distance between the probe 432 and the external focal plane 406. For example, the compact light focusing assembly 410 can be configured such that a change in the distance between the Z1 lens group 412 and the Z2 lens group 414 produces at least a 2-fold larger change in the separation between the probe 432 and the external focal plane 406. In many embodiments, the compact light focusing assembly 410 is configured such that a change in the distance between the Z1 lens group 412 and the Z2 lens group 414 produces at least a 4-fold larger change in the separation between the probe 432 and the external focal plane 406. FIGS. 8 and 9 illustrate similar concepts, with FIG. 9 having the probe added to demonstrate suitability to a very slim probe. FIG. 8 illustrates the optical extent that would be required without the use of the forward aperture concept.

Use of the compact light focusing assembly 410 may result in significant reduction in overall optical path length. The compact light focusing assembly 410 may provide a reduced optical path length (as compared to existing approaches) without compromising field of view (FOV).

Figure 10:
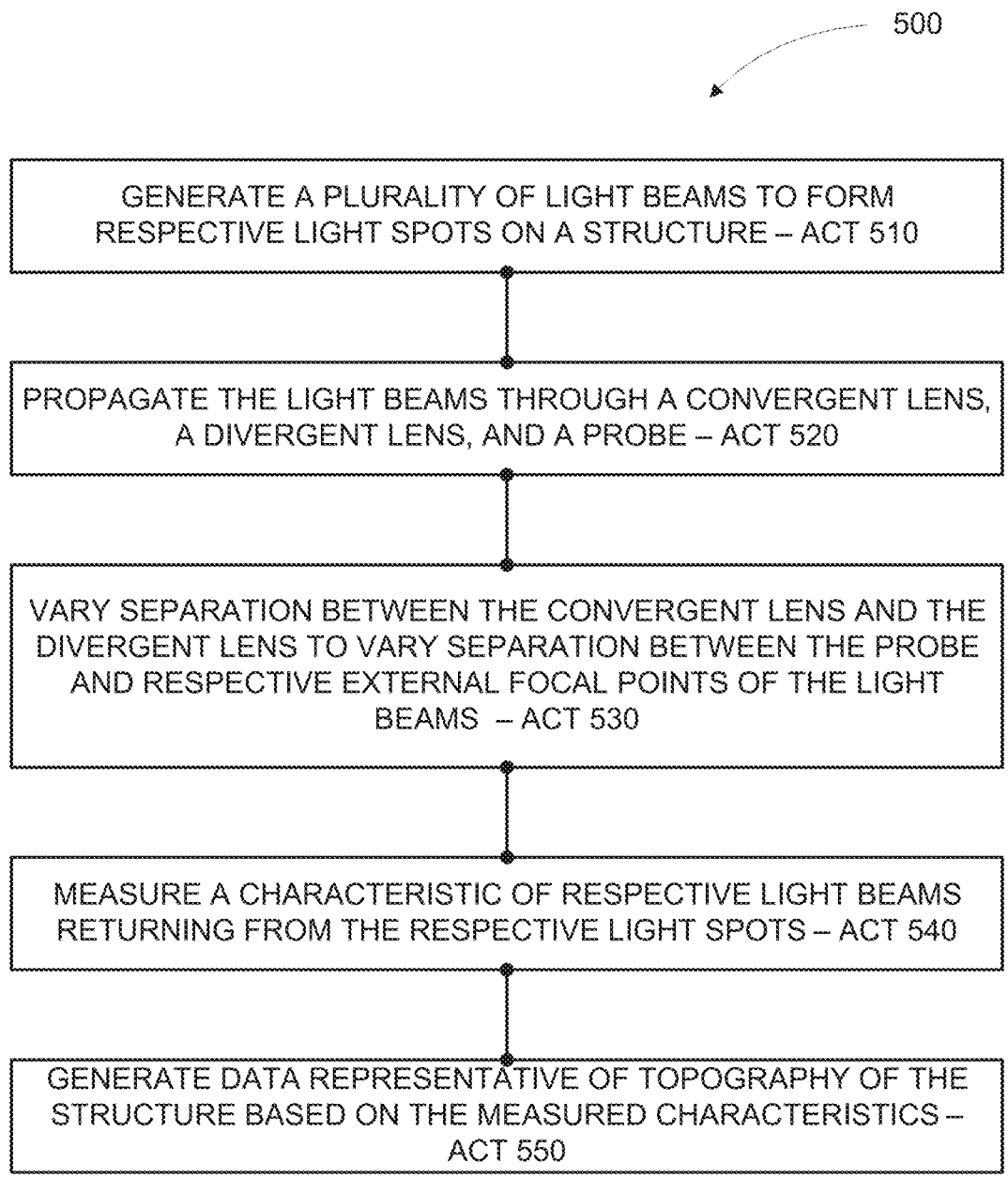
FIG. 10 is a simplified block diagram presenting acts of a method for determining surface topography of a three-dimensional structure, in accordance with many embodiments.

FIG. 10 illustrates acts of a method 500 for determining surface topography of a three-dimensional structure, in accordance with many embodiments. Any suitable optical assemblies, devices, apparatus, and/or systems, such as suitable embodiments described herein, can be used to practice the method 500.

In act 510, a plurality of light beams is generated. Any suitable device can be used to produce the light beams. For example, referring to FIG. 1A, the apparatus 20 can be used to produce the light beams. The apparatus 20 includes the grating or micro lens array 38, which splits the laser beam 30 emitted by light source 28 into an array of beams 36.

In act 520, the light beams are propagated through a convergent lens, a divergent lens, and a probe. Any suitable optics can be used to accomplish act 520. For example, the embodiments illustrated in FIG. 8 and FIG. 9 can be used to accomplish act 520.

In act 530, the separation between the convergent lens and the divergent lens is varied to vary the separation between the probe and the respective external focal points of the light beams. Referring, for example, to the embodiments illustrated in FIG. 9, the external focal points can form an external focal plane located exterior to the probe. The separation between the probe and the external focal plane can be increased by decreasing the separation between the convergent and divergent lenses. In some instances, the separation between the probe and the external focal points can be varied to scan the external focal plane through a plurality of focal depths. The separation can be oscillated by a suitable distance and at a suitable frequency, such as by the values previously provided herein with respect to the method 300. For example, the distance between the convergent and divergent lenses can be varied symmetrically by 1 mm, resulting in a 10 mm external focal plane shift.

In act 540, characteristics of the respective light beams returning from the respective light spots are measured. For example, as illustrated in FIG. 1A, the returning light beams 54 are reflected by the surface of the structure and each correspond to one of the incident light beams 36 produced by the optical device 22. Any suitable device can be used to measure the characteristics of the returning light beams, such as the sensor array 68.

In act 550, data representative of topography of the structure is generated based on the measured characteristics, as previously described herein. Any suitable device can be used to receive and generate the data, such as the processor 24 depicted in FIG. 1B.

Any suitable features of any of the embodiments of the assemblies, systems, methods, and devices described herein can be combined or substituted with any suitable features of other embodiments described herein. For example, the confocal optics 42 of the optical device 22 can include any of the light focusing assemblies described herein, such as any of the light focusing assemblies 220, 230, 410. In many instances, the exemplary optical systems described herein can be combined with a probe, such as the probing member 90, to facilitate optical measurement of the intraoral cavity. One of skill in the art will appreciate there are many suitable combinations and substitutions that can be made from the systems, methods, and devices described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for determining surface topography of a structure, the apparatus comprising:
    an illumination unit configured to output a plurality of light beams;
    a light focusing assembly comprising an image space lens, an object space lens and a focus changing assembly between the image space lens and the object space lens and being configured to:
        overlap the plurality of light beams within the light focusing assembly; and
        focus each of the plurality of light beams to a plurality of external focal planes to generate illuminated spots on the structure;
    a detector configured to measure a characteristic of a plurality of light beams returning from the illuminated spots on the structure; and
    a processor coupled to the detector and configured to generate data representative of topography of the structure based on the measured characteristic of each of the plurality of reflected light beams.

2. The apparatus of claim 1, wherein at least a portion of the focus changing assembly is located at a back focal length of an objective lens.

3. The apparatus of claim 1, wherein the focus changing assembly is located along optical paths of the plurality of light beams such that one or more of the plurality of light beams overlaps with one or more other light beams of the plurality of light beams along at least a portion of the focus changing assembly.

4. The apparatus of claim 1, wherein each of the plurality of light beams are substantially collimated upon entering the focus changing assembly and wherein the focus changing assembly adjusts each of the plurality of light beams to a convergent configuration, a collimated configuration, or a divergent configuration upon exiting the focus changing assembly.

5. The apparatus of claim 1, wherein the characteristic comprises an intensity of the reflected light beams.

6. The apparatus of claim 1, wherein the focus changing assembly moves the plurality of external focal planes at least 10 mm.

7. The apparatus of claim 1, wherein the object space lens comprises a telecentric lens and at least a portion of the focus changing assembly is located at a back focal length of the telecentric lens.

8. The apparatus of claim 1, wherein the image space lens comprises a focal length and location arranged to overlap and substantially collimate the plurality of light beams passing through the focus changing assembly.

9. The apparatus of claim 1, wherein the focus changing assembly comprises a variable optical power element and is operable to move the respective focal planes without movement of the variable optical power element, thereby oscillating the respective focal planes by a distance of at least 10 mm at a frequency greater than 10 Hz.

10. The apparatus of claim 1, wherein the focus changing assembly comprises a divergent lens and a convergent lens, and separation between the divergent lens and the convergent lens is varied to displace the external focal planes.

11. A method of determining surface topography of a structure, the method comprising:
    illuminating the structure using a light focusing assembly including an image space lens, an object space lens, and a focus changing assembly between the image space lens and the object space lens to overlap each of a plurality of light beams within the light focusing assembly and focus each of the plurality of light beams to a plurality of external focal planes to illuminate the structure; a portion of the focus changing assembly located at a back focal length of the object space lens and comprising a) a variable optical power element or b) a divergent lens and a convergent lens;
    operating the focus changing assembly to displace the respective focal planes to the plurality of external focal planes;
    measuring a characteristic of each of a plurality of light beams returning from the illuminated structure; and
    generating, with a processor, data representative of topography of the structure based on the measured characteristic.

12. The method of claim 11, wherein at least a portion of the focus changing assembly is located at a back focal length of an objective lens of the light focusing assembly.

13. The method of claim 11, wherein the focus changing assembly is located along optical paths of each of the plurality of light beams such that one or more of the plurality of light beams overlaps with one or more other light beams of each of the plurality of light beams along at least a portion of the focus changing assembly.

14. The method of claim 11, wherein each of the plurality of light beams are substantially collimated upon entering the focus changing assembly and wherein the focus changing assembly adjusts each of the plurality of light beams to a convergent configuration, a collimated configuration, or a divergent configuration upon exiting the focus changing assembly.

15. The method of claim 11, wherein the characteristic comprises an intensity of the returning light beams.

16. The method of claim 11, wherein the focus changing assembly moves the plurality of external focal planes at least 10 mm.

17. The method of claim 11, wherein the object space lens comprises a telecentric lens and at least a portion of the focus changing assembly is located at a back focal length of the telecentric lens.

18. The method of claim 11, wherein the image space lens comprises a focal length and location arranged to overlap and substantially collimate each of the plurality of light beams passing through the focus changing assembly.

19. The method of claim 11, wherein the focus changing assembly comprises the variable optical power element operable to move the respective focal planes without movement of the variable optical power element, thereby oscillating the respective focal planes by a distance of at least 10 mm at a frequency greater than 10 Hz.

20. The method of claim 11, wherein the focus changing assembly comprises the divergent lens and the convergent lens, and separation between the divergent lens and the convergent lens is varied to displace the plurality of external focal planes.

* * * * *